(12) United States Patent
Muñoz Sáez

(10) Patent No.: US 9,867,814 B2
(45) Date of Patent: Jan. 16, 2018

(54) USE OF NON-PEPTIDIC NK1 RECEPTOR ANTAGONISTS FOR THE PRODUCTION OF APOPTOSIS IN TUMOUR CELLS

(75) Inventor: Miguel Muñoz Sáez, Sevilla (ES)

(73) Assignee: NK-1 IP LIMITED, London (GB)

( * ) Notice: Subject to any disclaimer, the term of this patent is extended or adjusted under 35 U.S.C. 154(b) by 1867 days.

(21) Appl. No.: 11/721,256

(22) PCT Filed: Feb. 10, 2005

(86) PCT No.: PCT/ES2005/000068
§ 371 (c)(1),
(2), (4) Date: Sep. 16, 2008

(87) PCT Pub. No.: WO2005/077366
PCT Pub. Date: Aug. 25, 2005

(65) Prior Publication Data
US 2009/0012086 A1 Jan. 8, 2009

(30) Foreign Application Priority Data
Feb. 11, 2004 (ES) .................................. 200400424

(51) Int. Cl.
| | | |
|---|---|---|
| *A01N 43/00* | (2006.01) | |
| *A61K 31/33* | (2006.01) | |
| *A61K 31/451* | (2006.01) | |
| *A61K 31/445* | (2006.01) | |
| *A61K 38/04* | (2006.01) | |
| *A61K 31/4375* | (2006.01) | |
| *A61K 31/439* | (2006.01) | |
| *A61K 31/454* | (2006.01) | |
| *A61K 31/496* | (2006.01) | |
| *A61K 31/5377* | (2006.01) | |

(52) U.S. Cl.
CPC .......... *A61K 31/451* (2013.01); *A61K 31/439* (2013.01); *A61K 31/4375* (2013.01); *A61K 31/445* (2013.01); *A61K 31/454* (2013.01); *A61K 31/496* (2013.01); *A61K 31/5377* (2013.01); *A61K 38/046* (2013.01)

(58) Field of Classification Search
CPC .............. A61K 38/046; A61K 2300/00; A61K 31/4375; A61K 31/439; A61K 31/445; A61K 31/451; A61K 31/454; A61K 31/496; A61K 31/5377
USPC ........................................... 514/236.2, 255.01
See application file for complete search history.

(56) References Cited

U.S. PATENT DOCUMENTS 6,235,764 B1 * 5/2001 Larson et al. ................. 514/372
6,576,638 B1 6/2003 Pompei et al.
2003/0004157 A1 1/2003 Buser et al.
2003/0216430 A1 * 11/2003 Kawamura ................... 514/312

FOREIGN PATENT DOCUMENTS

| EP | 773026 | 11/1996 |
|---|---|---|
| EP | 0773026 | 5/1997 |
| EP | 773026 A2 * | 5/1997 |
| EP | 1 803 456 | 7/2007 |
| WO | WO 9218536 A2 * | 10/1992 |
| WO | WO 98/54116 | 12/1998 |
| WO | WO9854116 | * 12/1998 |
| WO | WO 9854116 | 12/1998 |
| WO | WO 01/01922 | 1/2001 |
| WO | WO 0101922 | 1/2001 |
| WO | 2006/111169 A1 | 10/2006 |
| WO | WO 2009/124756 | 10/2009 |

OTHER PUBLICATIONS

Saretzki et al (hTERT gene dosage correlates with telemerase activity in human lung cancer cell lines, Cancer letters 176, 2002, 81-91).*
Kramer et al "Demonstration of the efficacy and safety of a novel substance P (NK1) receptor antagonist in major depression" Neuropsychopharmacology (2004), published online Jun. 9, 2003, vol. 29, pp. 385-392.*
ICLC database http://wwwsql.iclc.it/test/iclc/, accessed on Jun. 3, 2014.*
Bosserhoff et al, the Journal of Biological Chemistry, vol. 278, No. 17, Issue of Apr. 25, pp. 15225-15231.*
Mayer et al, FEBS, Letters 480 (2000) 156-160.*
Munoz et al, Expert Opinion on Drug Safety, vol. 12, 2013, Issue 5, pp. 673-685.*
Rosso et al, Scientific World Journal. 2012; pp. 1-21.*
Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Muñoz , M. et al: "Antitumoral action of L-733.060 on neuroblastoma and glioma cell lines". Archives Italiennes de Biologie, Mar. 2004, vol. 142 (2), pp. 105-112.
Muñoz , M. et al.: "antitumoral action of the neurokinin-1 receptor antagonist L-733060 on human melanoma cell lines". Melanoma Research, Jun. 2004, vol. 14(3), pp. 183-188.
International Search Report PCT/ES2005/000068 dated May 23, 2005.
G. Giardina et al., "Antagonists at the neurokinin receptors—Recent patent literature", *Idrugs*, 6(8):758-772 (2003).
M. Kramer et al., "Distinct Mechanism for Antidepressant Activity by Blockade of Central Substance P Receptors", *Science*, 281:1640-1645 (1998).
P. Murtra et al., "Rewarding effects of opiates are absent in mice lacking the receptor for substance P", *Nature*, 405:180-183 (2000).
P. Bunn et al., "Effects of Neuropeptide Analogues on Calcium Flux and Proliferation in Lung Cancer Cell Lines", *Cancer Research*, 54:3602-3610 (1994).

(Continued)

*Primary Examiner* — Jean P Cornet
(74) *Attorney, Agent, or Firm* — McNeill Baur PLLC

(57) ABSTRACT

The invention relates to the use of substance P antagonists and, in particular, the use of non-peptidic NK1 receptor antagonists for the treatment of cancer and, more specifically, human melanoma, neuroblastoma, glioma, human Hodgkin's lymphoma KM-H2, lymphoblastic leukaemia, human rhabdomyosarcoma, human breast carcinoma, human Burkitt's lymphoma, human lung carcinoma, human Ewing's sarcoma, human glioma and human osteosarcoma.

4 Claims, 10 Drawing Sheets

(56) References Cited

OTHER PUBLICATIONS

R. Navari et al., "Reduction of Cisplatin-Induced Emesis by a Selective Neurokinin-1-Receptor Antagonist", *The New England Journal of Medicine*, 190-195 (1999).

J. Longmore et al., "Neurokinin-receptor antagonists: pharmacological tools and therapeutic drugs", *Can. J. Physiol*, 75:612-621 (1997).

C. A. Maggi et al., "Tachykinin receptors and tachykinin receptor antagonists", *Tachykinin Receptors*, pp. 24-93.

T. Doi et al., "Effects of TAK-637, a tachykinin receptor antagonist, on lower urinary tract function in the guinea pig", *European Journal of Pharmacology*, 383:297-303 (1997).

M. Munoz et al., "Antitumoural Action of L-733,060 on Neuroblastoma and Glioma Cell Lines", *Archives . . . de Biologia*, 142:105-112.

M. Munoz et al., "Antitumoural action of the neurokinin-1 receptor antagonist L-733 060 on human melanoma cell lines", *Melanoma Research*, 14(3):153-158 (2004).

A. Orosz et al., New Short-Chain Analogs of a Substance-P1 Antagonist Inhibit Proliferation of Human Small-Cell Lung-Cancer Cells In-Vitro and In-Vivo, *Int. J. Cancer*,60:82-87 (1995).

C. Palma et al., "The role of tachykinins via NK1 receptors in progression of human gliomas", *Life Sciences*, 67:985-1001 (2000).

L. Quartara et al., "The tachykinin NK1 receptor. Part II: distribution and pathophysiological roles", *Neuropeptides*, 32(1):1-49 (1998).

R. Baker, "Tachykinins, Neurotrophism and Neurodegenerative Diseases: A Critical Review on the Possible Role of Tachykinins in the Aetiology of CNS Diseases", *Reviews in the Neurosciences*, 7:187-214 (1996).

Hafizi et al., "Neurokinin-1 receptor antagonists as novel antidepressants: trials and tribulations", British Journal of Psychiatry, vol. 191, pp. 282-284, 2007.

Marriott et al., The Role of Tachykinins in Central Nervous System Inflammatory Responses, Frontiers in Bioscience, vol. 9, pp. 2153-2165, 2004.

Palma et al., "Correlation between binding characteristics and functional antagonism in human glioma cells by tachykinin NK1 receptor antagonists", European Journal of Pharmacology, vol. 374, Issue 3, pp. 435-443, 1999.

Palma et al., "Anti-tumour activity of tachykinin NK1 receptor antagonists on human glioma U373 MG xenograft", British Journal of Cancer, vol. 82, No. 2, pp. 480-487, 2000.

Friess et al., "Neurokinin-1 Receptor Expression and Its Potential Effects on Tumor Growth in Human Pancreatic Cancer", Laboratory Investigation, vol. 83, No. 5, pp. 731-742, 2003.

Aprepitant Drug Monograph: National PBM Drug Monograph, "Aprepitant (Emend)", pp. 1-21, 2003.

Chawla et al., "Establishing the dose of the oral NK1 antagonist aprepitant for the prevention of chemotherapy-induced nausea and vomiting", PubMed, Cancer, vol. 97, No. 9, pp. 290-300, 2003.

Herpfer et al., "Substance P receptor antagonists in psychiatry: rationale for development and therapeutic potential", PubMed, CNS Drugs, vol. 19, No. 4, pp. 275-293, 2005.

Rost et al., "[Neurokinin 1 receptor antagonists—between hope and disappointment]", PubMed, Med Monatsschr Pharm., vol. 29, No. 6, pp. 200-205, 2006.

Annals of Oncology, "Antiemetic neurokinin-1 antagonist aprepitant and ifosfamide-induced encephalopathy", Letters to the editor, vol. 18, No. 4, 2007.

Gore et al., "Aprepitant in adolescent patients for prevention of chemotherapy induced nausea and vomiting: a randomized, double-blind, placebo-controlled study of efficacy and tolerability", PubMed, Pediatr Blood Cancer, vol. 52, No. 2, pp. 242-247, 2009.

Jarkowski, A., "Possible contribution of aprepitant to ifosfamide-induced neurotoxicity", PubMed, Am J Health Syst Pharm, vol. 65, No. 23, pp. 2229-2231, 2008.

Duffy, RA., "Potential therapeutic targets for neurokinin-1 receptor antagonists", PubMed, Expert Opin Emerg Drugs, vol. 9, No. 1, pp. 9-21, 2004.

Munoz et al., "Antitumoral action of the neurokinin-1 receptor antagonist L-733 060 on human melanoma cell lines", PubMed, Melanoma Res., vol. 14, No. 3, pp. 183-188, 2004.

Munoz et al., "The NK1 receptor is involved in the antitumoural action of L-733,060 and in the mitogenic action of substance P on neuroblastoma and glioma cell lines", PubMed, Neuropeptides, vol. 39, No. 4, pp. 427-432, 2005.

Warr, D., "The neurokinin1 receptor antagonist aprepitant as an antiemetic for moderately emetogenic chemotherapy", PubMed, Expert Opin Pharmacother, vol. 7, No. 12, pp. 1653-1658, 2006.

Palma, C. "Tachykinins and their receptors in human malignancies", PubMed, Curr Drug Targets, vol. 7, No. 8, pp. 1043-1052, 2006.

Rameshwar, P., "Implication of possible therapies targeted for the tachykinergic system with the biology of neurokinin receptors and emerging related proteins", PubMed, Recent Pat CNS Drug Discov, vol. 2, No. 1, pp. 79-84, 2007.

Patacchini et al., "Characterization of receptors mediating contraction induced by tachykinins in the guinea-pig isolated common bile duct", PubMed, Br J Pharmacol, vol. 122, No. 8, pp. 1633-1638, 1997.

Cirillo, R., "Pharmacology of the peptidomimetic, MEN 11149, a new potent, selective and orally effective tachykinin NK1 receptor antagonist", PubMed, Eur J Pharmacol, vol. 341, No. 2-3, pp. 201-209, 1998.

Cirillo, R., "Pharmacology of MEN 11467: a potent new selective and orally effective peptidomimetic tachykinin NK (1) receptor antagonist", PubMed, Neuropeptides, vol. 35, No. 3-4, pp. 137-147, 2001.

M. Munoz, et al: "The NK1 Receptor is Involved in the Antitumoural Action of L-733,060 and in the Mitogenic Action of Substance P on Neuroblastoma and Glioma Cell Lines", Neuropeptides 39 (2005) 427-432.

M. Munoz, et al: "Antitumoral Action of the Neurokinin-1-Receptor Antagonist L-733,060 and Mitogenic Action of Substance P on Human Retinoblastoma Cell Lines", IOVS, Jul. 2005, vol. 16, No. 7.

Japanese Office Action and Translation thereof, Japanese Patent Application No. JP2006-335507, dated Mar. 5, 2012.

German Search Report EP 14189674, dated Feb. 17, 2015.

Munoz et al: "A New Frontier in the Treatment of Cancer: NK-1 Receptor Antagonists", Current Medicinal Chemistry, vol. 17, No. 6, Jan. 1, 2010, pp. 504-516.

Harford-Wright et al: "Evaluating the Role of Substance P in the Growth of Brain Tumors", Neuroscience, vol. 261, 2014, pp. 85-94.

Navari: "Pathogenesis-Based Treatment of Chemotherapy-Induced Nausea and Vomiting—Two New Agents", www.supportiveoncology.net, vol. 1, No. 2, Jul./Aug. 2003, pp. 89-103.

"Aprepitant", On the Horizon Future Medicines, National Prescribing Centre, Liverpool UK, XP-002735359, Monograph 1 (2004).

Alcaide et al., "The role and prognostic value of apoptosis in colorectal carcinoma," BMC Clinical Pathology 2013, 13:24, pp. 1-7, http://www.biomedcentral.com/1472-6890/13/24.

Berger et al., "Hepatoblastoma cells express truncated neurokinin-1 receptor and can be growth inhibited by aprepitant in vitro and in vivo," Journal of Hepatology, vol. 60, No. 5, May 2014, pp. 1-11.

Brener et al., "A Role for the Substance Pink-1 Receptor Complex in Cell Proliferation in Oral Squamous Cell Carcinoma," Anticancer Research 29:2323-2330, 2009.

Covenas et al., "Cancer progression and substance P," Histol Histopathol (2014) 29:881-890.

Esteban et al. "Expression of substance P and neurokinin-1-receptor in laryngeal cancer: linking chronic inflammation to cancer promotion and progression," Histopathology 2009, 54, pp. 258-269.

Esteban et al., "A role for substance P in cancer promotion and progression: a mechanism to counteract intracellular death signals following oncogene activation or DNA damage," Cancer Metastasis Rev., 2006, 25:137-145.

Gonzalez Moles et al., "A role for the substance P/NK-1 receptor complex in cell proliferation and apoptosis in oral lichen planus," Oral Diseases (2009) 15, pp. 162-169.

Gonzalez Moles et al., "Cell proliferation associated with actions of the substance P/NK-1 receptor complex in keratocystic odontogenic tumours," Oral Oncology, 2008, 44, pp. 1127-1133.

(56) References Cited

OTHER PUBLICATIONS

Gonzalez-Ortega et al. "Uveal melanoma expresses NK-1 receptors and cyclosporin A induces apoptosis in human melanoma cell lines overexpressing the NK-1 receptor," Peptides 55 (2014), pp. 1-12.
Kast et al., "A conceptually new treatment approach for relapsed glioblastoma: Coordinated undermining of survival paths with nine repurposed drugs (CUSP9) by the International Initiative for Accelerated Improvement of Glioblastoma Care," Oncotarget, 2013, vol. 4, No. 4, pp. 502-530.
Munoz et al., "A New Frontier in the Treatment of Cancer: NK-1 Receptor Antagonists," Current Medicinal Chemistry, 2010, vol. 17, No. 1, pp. 1-13.
Munoz et al., "A Therapeutic Target in Leukemia: The NK-1 Receptor," Acute Lymphoblastic Leukemia, Chapter VI, ISBN 978-1-61470-872-8, 2011, pp. 1-17.
Munoz et al., "Antitumor activity of neruokinin-1 receptor antagonists in MG-63 human osteosarcoma xenografts," International Journal of Oncology 44: 137-146, 2014.
Munoz et al., "Antitumoral Action of the Neurokinin-1-Receptor Antagonist L-733,060 and Mitogenic Action of Substance P on Human Retinoblastoma Cell Lines," IOVS, Jul. 2005, vol. 46, No. 7, pp. 2567-2570.
Munoz et al., "Antitumoural Action of L-733,060 on Neuroblastoma and Glioma Cell Lines," Archives Italiennes de Biologie, 142:105-112, 2004.
Munoz et al., "Antitumoural Action of Neurokinin-1 Receptor Antagonists on Human Brain Cancer Cell Lines," Brain Cancer: Therapy and Surgical Interventions, Chapter III, ISBN 1-59454-974-5, 2006, pp. 1-32.
Munoz et al., "Immunolocalization of NK-1 Receptor and Substance P in Human Normal Placenta," Placenta 31 (2010), pp. 649-651.
Munoz et al., "Immunolocalization of Substance P and NK-1 Receptor in Hofbauer Cells in Human Normal Placenta," Microscopy Research and Technique 76:1310-1313, 2013.
Munoz et al., "Immunolocalization of the Neurokinin-1 Receptor: A new Target in the Treatment of the Human Primary Retinoblastoma," Eye Cancer Research Progress, ISBN 978-1-60456-045-9, 2008, pp. 1-22.
Munoz et al., "Involvement of substance P and the NK-1 receptor in cancer progression," Peptides 48 (2013), pp. 1-9.
Munoz et al., "Involvement of substance P and the NK-1 receptor in human pathology," Amino Acids, 2014, DOI 10.1007/s00726-014-1736-9, pp. 1-26.
Munoz et al., "Involvement of substance P and the NK-1 receptor in pancreatic cancer," World J Gastroenterol, Mar. 7, 2014, 20(9): 2321-2334.
Munoz et al., "Neurokinin-1 receptor antagonists and cancer," Focus on Neuropeptide Research, 2007:341-362, ISBN: 978-81-7895-291-8.
Munoz et al., "Neurokinin-1 Receptor: A New Promising Target in the Treatment of Cancer," Discovery Medicine, vol. 10, No. 53, pp. 305-313, Oct. 2010.
Munoz et al., "Neurokinin-1 Receptors Located in Human Retinoblastoma Cell Lines: Antitumor Action of Its Antagonist, L-732,138," Investigative Ophthalmology & Visual Science, Jun. 2007, vol. 48, No. 6, pp. 2775-2781.
Munoz et al., "Neuropeptides and Cancer: Focus on Substance P/Neurokinin-1 Receptor System Research," Neuropeptide Research Trends, Chapter V, ISBN: 978-1-60021-640-4, pp. 1-23.
Munoz et al., NK-1 receptor antagonists as antitumor drugs: a survey of the literature from 2000 to 2011, Expert Opin. Ther. Patents (2012), 22(7), pp. 735-746.
Munoz et al., "NK-1 Receptor Antagonists as New Anti-Tumoural Agents: Action on Human Neuroblastoma Cell Lines," Focus on Neuroblastoma Research, ISBN 1-60021-484-3, 2007, pp. 1-27.
Munoz et al., "NK-1 receptor antagonists include apoptosis and counteract substance P-related mitogenesis in human laryngeal cancer cell line HEp-2," Invest New Drugs, 2008, 26:111-118.
Munoz et al., "NK-1 Receptor Antagonists: A New Generation of Anticancer Drugs," Mini-Reviews in Medicinal Chemistry, 2012, vol. 12, No. 6, pp. 1-7.
Munoz et al., "NK-1 Receptor Antagonists: A New Paradigm in Pharmacological Therapy," Current Medicinal Chemistry, 2011, vol. 18, No. 12, pp. 1820-1831.
Munoz et al., "Paravertebral anesthesia: how substance P and the NK-1 receptor could be involved in regional block and breast cancer recurrence," Breast Cancer Res. Treat (2010) 122:601-603.
Munoz et al., "Safety of neurokinin-1 receptor antagonists," Expert Opin. Drug Saf. (2013) 12(5), pp. 1-13.
Munoz et al., "Substance P, the NK-1 Receptor and NK-1 Receptor Antagonists in Cancer Treatment," Frontiers in Anti-Cancer Drug Discovery, vol. 4, 2014, pp. 3-38.
Munoz et al., "Targeting NK-1 Receptors to Prevent and Treat Pancreatic Cancer: a New Therapeutic Approach," Cancers 2015, 7, pp. 1215-1232.
Munoz et al., "The Antiproliferative Action of [D-Arg1, D-Phe5, D-Trp7,9, Leu11] Substance P Analogue Antagonist Against Small Cell- and Non-Small-Cell Lung Cancer Cells Could be due to the Pharmacological Profile of its Tachykinin Receptor Antagonist," Journal of Physiology and Pharmacology 2015, 66, 33, pp. 421-426.
Munoz et al., "The broad-spectrum antitumor action of cyclosporin A is due to its tachykinin receptor antagonist Pharmacological profile," Peptides 31 (2010), pp. 1643-1648.
Munoz et al., "The neurokinin-1 receptor antagonist aprepitant is a promising candidate for the treatment of breast cancer," International Journal of Oncology, DOI: 10.3892/ijo.2014.2565, 2014, pp. 1-15.
Munoz et al., "The NK-1 receptor antagonist aprepitant as a broad spectrum antitumor drug," Invest New Drugs (2010) 28:187-193.
Munoz et al., "The NK-1 Receptor Antagonist L-732,138 Induces Apoptosis and Counteracts Substance P-Related Mitogenesis in Human Melanoma Cell Lines," Cancers 2010, 2, 611-623.
Munoz et al., "The NK-1 receptor is expressed in human leukemia and is involved in the antitumor action of aprepitant and other NK-1 receptor antagonists on acute lymphoblastic leukemia cell lines," Invest New Drugs (2012) 30:529-540.
Munoz et al., "The NK-1 receptor is expressed in human melanoma and is involved in the antitumor action of the NK-1 receptor antagonist aprepitant on melanoma cell lines," Laboratory Investigation (2010) 90, pp. 1259-1269.
Munoz et al., "The NK1 receptor is involved in the antitumoural action of L-733,060 and in the mitogenic action of substance P on neuroblastoma and glioma cell lines," Neuropeptides 39, 2005, pp. 427-432.
Munoz et al., "The NK-1 Receptor is Involved in the Antitumoural Action of L-733,060 and in the Mitogenic Action of Substance P on Human Pancreatic Cancer Cell Lines," Letters in Drug Design & Discovery, 2006, vol. 3, No. 5, pp. 1-7.
Munoz et al., "The NK-1 Receptor: A New Target in Cancer Therapy," Current Drug Targets, 2011, vol. 12, No. 6, pp. 909-921.
Munoz et al., "The substance P/neurokinin-1 receptor system in lung cancer: Focus on the antitumor action of neurokinin-1 receptor antagonists," Peptides 38 (2012), pp. 318-325.
Munoz et al., "The substance P/NK-1 receptor system: NK-1 receptor antagonists as anti-cancer drugs," J. Biosci. 40 (2), Jun. 2015, pp. 441-463.
Munoz, et al., "Antitumoral action of the neurokinin-1 receptor antagonist L-733 060 on human melanoma cell lines," Melanoma Research, 2004, vol. 14, No. 3, 183-188.
Rosso et al., "The NK-1 Receptor is Expressed in Human Primary Gastric and Colon Adencarcinomas and is Involved in the Antitumor Action of L-733,060 and the Mitogenic Action of Substance P on Human Gastrointestinal Cancer Cell Lines," Tumor Biol. 934, 2008, pp. 1-10.
Rosso et al., "The Role of Neurokinin-1 Receptor in the Microenvironment of Inflammation and Cancer," The Scientific World Journal, vol. 2012, article ID 381434, pp. 1-21.

* cited by examiner

USE OF NON-PEPTIDIC NK1 RECEPTOR ANTAGONISTS FOR THE PRODUCTION OF APOPTOSIS IN TUMOUR CELLS

CROSS REFERENCE TO RELATED APPLICATION

The present application is a 35 U.S.C. §371 national phase conversion of PCT/ES2005/000068, filed Feb. 10, 2005, which claims priority of Spanish Patent Application No. P200400424 filed Feb. 11, 2004, which is herein incorporated by reference. The PCT International Application was published in the Spanish language.

FIELD OF THE INVENTION

The invention involves the use of P substance antagonists, specifically non-peptide NK1 receptor antagonists, in the treatment of human cancers, explicitly on melanoma, neuroblastoma, glioma, Hodgkin's-KM-H2 lymphoma, lymphoblastic leukemia, Rhabdomyosarcoma, breast cancer, Burkitt's lymphoma, lung cancer, Edwing's sarcoma and human osteosarcoma.

BACKGROUND OF THE INVENTION

The P substance is a natural undecapeptide from the Tachykinins family and is used for its rapid stimulant action on smooth muscle tissue. More specifically, the P substance is an active pharmacological neuropeptide that is produced in mammals. It was originally isolated in the intestine and possesses an amino acid sequence that has been described by D. F. Veber, in the patent U.S. Pat. No. 4,680,283. The implication of the P substance, like in other Tachykinins, is seen in the physiopathology in a large number of illnesses that are well demonstrated in the bibliography.

The P substance receptor is a member of the super family of G-protein-coupled receptors. The neuropeptide receptor of the P (NK-1) substance is well distributed in the nervous system of mammals (especially in the cerebrum and spinal cord) the circulatory system and in the peripheral tissues (especially in the duodenum and in the jejunum) and is involved in the regulation of diverse biological processes.

The central and peripheral action of the Tachykinins in mammals have been associated with various inflammatory conditions such as migraines, rheumatoid arthritis, asthma, and intestinal inflammatory disease, as well as in the mediation of nauseous reflexes, and the regulation of CNS central nervous system disorders such as Parkinson's disease. (Neurosci. Res., 1996, 7, 187-214), anxiety (Can. J. Phys.; 1997, 612-621) and depression (Science, 1998, 281, 1640-1645).

In the article titled "Tachykinin Receptor and Tachykinin Receptor Antagonists", by J. Auton, in Pharmacol.; 1993, 13, 23-93, the use of antagonists of the P substance have been evidenced in the treatment of headaches, especially migraines, Alzheimer's disease, multiple sclerosis, attenuation of the syndrome in the absence of opiates, cardio vascular changes, edemas, such as those provoked by burns, in chronic inflammatory illnesses like rheumatoid arthritis, asthma, hyperactive bronchials, and other respiratory illnesses including allergic rhinitis, etc.

Also, U.S. Pat. No. 5,972,938 describes a method for the treatment of a psychoimmunological disorder or psychomotor by way of the administration of an NK1 receptor antagonist.

The article published in Nature, 2000,405 (6783), 180-183 details the activity in rats lacking NK-1 receptors and shows a decrease in the beneficial effects of morphine. Consequently, the NK-1 antagonist receptors can be used in the treatment of breaking certain drug addition habits such as those associated with opiates, nicotine as well as in the reduction of abuse and abstinence from the drugs.

The article in Life Sci.; 2000, 67(9), 985-1001 describes the Astrocytes express functional receptors for various neurotransmitters in the reception of the P substance. The cerebral tumors of malignant glials derived from Astrocytes unchain under the action of the Tachykinins mediating the NK-1 receptors in the secretion of soluble mediators that augment the speed of reproliferation. Consequently, the selective antagonists of NK-1 can be very useful therapeutic agents in the treatment of malignant gliomas and for the treatment of cancer.

Additionally, the New Journal of Medicine, 1999, 340, 190-195, states that the use of a selective NK1 receptor induces the reduction of vomiting by employing cisplatin.

In the article published in the International Journal of Cancer by Antal Orosz et al. 1995, 60, 82-87, the use of diverse peptide antagonists in the P substance (SP) is described in the inhibition of the proliferation of lung cancer cells. (Ex. in designated cells NCI-H69). Equally as important is the article published in Cancer Research, 1994, 54, 3602-3610, describing another antagonist of the SP as well as other peptides capable of the inhibition of the growth of various in-vitro lines in cancerous lung cells (ex. Designated cells NCI-H510, NCI-H345, and SHP-77).

The patent EP 773026 (Pfizer) states the use of non-peptide NK1 receptor antagonists in the treatment of breast cancer, particularly in the treatment of small lung cancers in APUdoma, neuro endocrinic tumors, and small extra lung carcinomas.

Additionally in the WO 2001001922 patent the use of NK1 receptors in the treatment of adenocarcinoma is described, most specifically in prostatic carcinomas. Giardina, G.; Gagliardi S. and Martinelli M. review the most recent patents about the NK1, NK2 and NK3 receptors in "Antagonists at the neurokinin receptors-Recent patent literature" (IDrugs 2003; 6 (8): 758-772). The authors describe the action of the molecules of the most important world producers with a specific indication of the most noteworthy possible applications being used in the treatment of: depression, inflammation, anxiety, vomiting, Ulcerative colitis and other illnesses.

SUMMARY OF THE INVENTION

The objective of the current invention is the use of non-peptide NK1 receptor antagonists and the P substance for the production of apoptosis in breast cancer tumors. The tumor cells that the antagonists act on present a number of NK1 receptors that is superior to those in non tumor cells, composed of between 400% and 500% of the normal number of non tumor cells.

The tumor cells that the antagonists act on are selected between invasive primary and invasive malignant melanomas; metastatic melanoma cells; cells localized in ganglion lymph nodes; glioma cells; human breast cancer cells; Acute lymphoblastic leukemia B cells; Acute lymphoblastic leukemia T cells; primary neuroblastoma cells; astrocytoma cells; Burkitt's lymphoma cells; Hodgkin's lymphoma cells; Rhabdomyosarcoma cells; small lung cancer cells; Edwing's sarcoma cells; and osteosarcoma cells. They indicated the continuation in specific cells acted upon by the non-peptide NK1 receptor antagonists and the P substance.

The tumor cells related with human melanoma on which the current antagonists act in cellular lines are COLO 858 [ICLC, Interlab Cell Line Collection, CBA, Génova), MEL HO [DSMZ, Deutsche Sammlung von Mikroorganismen and Zellkulturen] and COLO 679 [DSMZ].

The tumor cells related with the human glioma and the human neuroblastoma to which the antagonists act on in cellular lines are the GAMG [DSMZ] and SKN-BE (2) [ICLC].

The tumor cells related with lymphoblastic leukemia which the current antagonists act on are human lymphoblastic leukemia cells B SD1 [DSMZ] and human lymphoblastic leukemia cells TBE-13 [DSMZ]. The tumor cells related with Burkitt's lymphoma on which the antagonists act in cellular lines are CA-46 [DSMZ]. The tumor cells related with Hodgkin's lymphoma on which the antagonists act are KM-H2 [DSMZ]. The tumor cells related with rabdomio human sarcoma on which the antagonists act in a cellular linear form are A-204 [DSMZ]. The tumor cells related with small human lung cancer cells on which the antagonists act in a cellular line are COLO-677 [DSMZ]. The tumor cells related with human breast cancer on which the antagonists act in a cellular line are MT-3 [DSMZ].

The tumor cells related with Edwing's sarcoma on which the current antagonists act in a cellular line are MHH-ES-1 [DSMZ].

The tumor cells related with human osteosarcoma on which the current antagonists act in a cellular line are MG-63 [ICLC].

One of the antagonists used is (2S,3S) 3-{[3,5-Bis(trifluoromethyl)phenyl]metoxi}-2-phenylpiperidine, commercially known as L-733060 (Sigma-Aldrich) and used in concentrations composed of between 5 suM and 50 I1M.

Other compounds of antagonist non-peptide receptors NK1 and the P substance that can be used include: vofopitant6GR-205171 (Pfizer), eziopitant 6 CJ-11974 (Pfizer), CP-122721 (Pfizer), Aprepitant 6 MK 869 6 L-754030 (MSD), L-758298 (MSD), TAK-637 (Takeda/Abbot), GW597599 (GSK), GW679769 (GSK), and R673 (Roche).

Lastly, the other objective on the current invention is the use of the non-peptide NK1 receptor antagonists and the P substance, such as the aforementioned indicators in the creation of a pharmaceutical composition for the treatment of cancer.

DETAILED DESCRIPTION OF THE INVENTION

Figure 1:
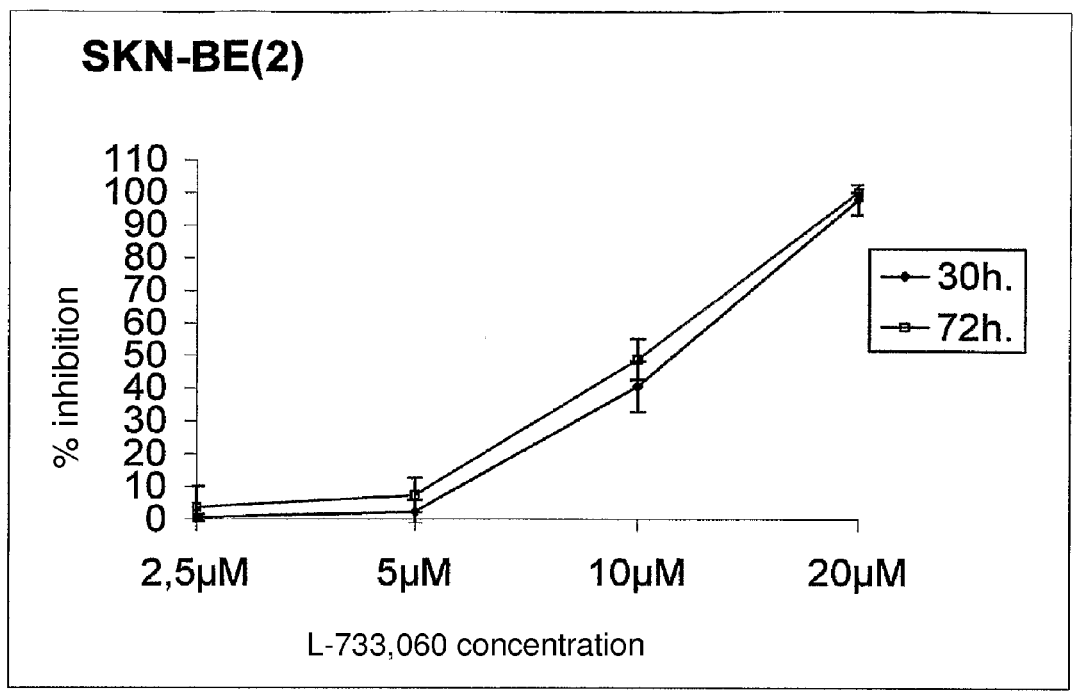
FIGS. 1A and 1B: variation in the time of the concentration of the cells SKN-BE (2) to growing concentrations of L-733,060(1A) in the cellular growth inhibition of SKN-BE (2)(1 B).
Figure 1:
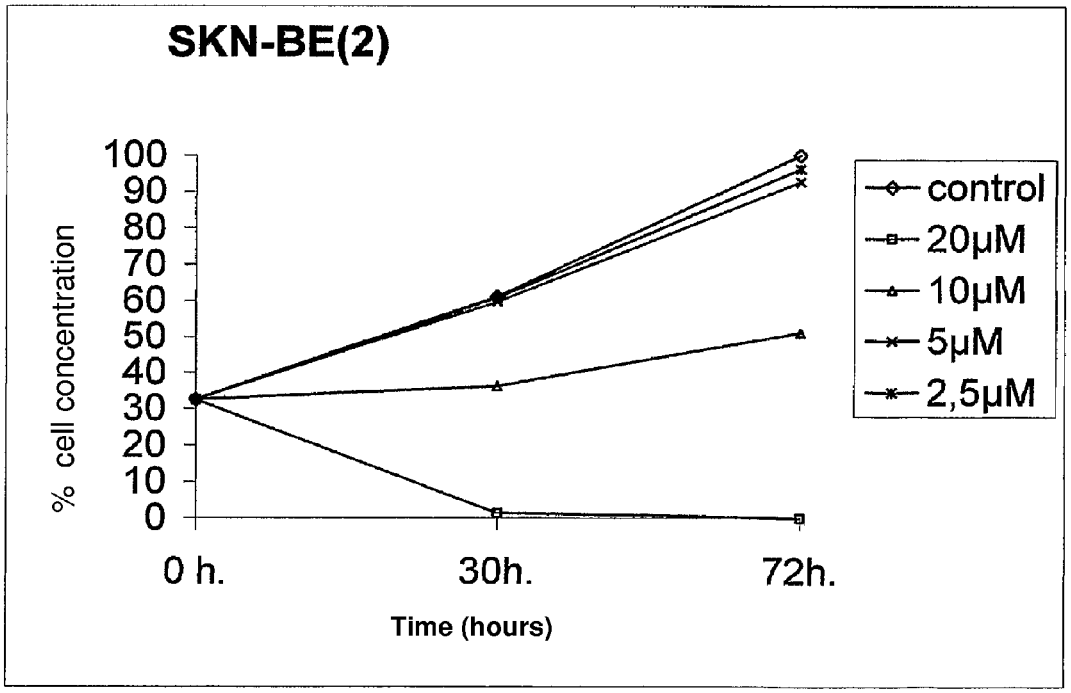

A detailed explanation of how the activity was carried out was based on testing of aspects of the current invention in various cellular lines. The following examples are provided only in order to illustrate the invention and thus they should not be construed as limiting.

Example 1

Cellular lines related with neuroblastoma: Cellular lines of human neuroblastoma SKN-BE (2)(ICLC Interlab Cell Line Collection-CBA-Genova) was used.

This line was maintained in a culture of RPMI 1640 (GIBCO-BRL) supplemented with 10% fetal bovine serum according to the established cellular culture conditions of the ATCC.

The cellular line was cultivated in flasks of 75 ml (Falcon, Germany). Half was refreshed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with the NK1 receptor antagonists: The solutions of antagonist NK1 receptors (2S,3S)3-([3,5Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 20 µM) were studied with the objective of determining the IC50.

The proliferation of cells was tested using the MTS [3-(4,5-dimethylthiazol-2il)-5-(3-carboxymethoxyphenyl) 2-(4-sulfophenyl)-2H-tetrazolium]method, following the instructions established by the manufacturer (CellTiter 96 Aqueous One Solution Cell Proliferation Assay, Promega, (USA).

Methods of cellular proliferation: During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 µl of MTS was immediately added to the wells and the wells were read 90 minutes later. T1 and T2 were treated with different concentrations of (2.5 µM to 20 µM) of L-733,060 and were incubated during a period of 30 hrs. (first cellular duplication) (T1) and 72 hrs. (second cellular duplication) (T2).

To study the proliferation of the cells 20 µl of MTS reactor was added to each well (T1,T2) 90 min., before reading the samples with the plate reader (TECAN Spectra Classic) at 492 nm. The reactive quantity of MTS, was measured by testing the optical density, being directly proportional to the number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on an adequate curve based on the parameters.

Statistical Analysis: The data obtained was evaluated using Student's t-test, with a significance level of $P<0.05$. Results: The results shown in FIG. 1A represent the variation in time of the concentration of cells SKN-BE (2) at growing concentrations of L-733,060.

The FIG. 1B shows the inhibition of cellular growth of SKNBE (2) (at 30 hrs. and 72 hrs.) after the addition of growing concentrations of L-733,060 (2.5, 5, 10, 20 µM) vs. the percentage of the inhibition in the first and second time in the duplication of the incubation. The non-continuous lines represent IC50 at 30 and 72 hrs. The points on the graph represent the average value/typical deviation.

Example 2

Cellular lines related with melanomas Cellular lines related with melanomas COLO 858 (ICLC Interlab Cell LineCollection-CBA-Genova), MEL HO and COLO 679 (DSMZ, Deutsche Sammlung von Mikroorganismen and Zellkulturen) were used.

This cellular line was maintained in a culture of RPMI 1640 (GIBCO BRL) supplemented with 10% fetal bovine serum according to the established cellular culture conditions of the ATCC, the ICLC and the DSMZ.

The cellular lines were cultivated in flasks of 75 ml (Falcon, Germany).

Half was renewed every two days and the cells were treated with Trypsin (0.05% and 0.02% EDTA without Ca2+ and Mg2+) every six days. The cells were incubated at 37 C in a humidification of (95% air/5% CO2).

The treatment with NK7 receptor antagonists (2S,3S) 3-([3,5 Bis(trifluoromethyl)phenyl]metoxi)-2-phenylpiperidine (L-733,060) (Sigma-Aldrich, U. K.) was dissolved in distilled water containing 0,2% dimethyl sulfoxide (DMSO) before treating the samples. With the objective of determining the IC50, different concentrations (2.5 µM to 50 µM) were studied.

The cellular proliferation was evaluated using the MTS method [3-(4,5-dimethylthiazol-2-il)-5-(3-carboxymethoxyphenyl) 2-(4-sulfophenyl)-2H-tetrazolium], according to the instructions of use established by the manufacturer (CellTiter 96 Aqueous One Solution Cell Proliferation Assay, Promega, USA).

Cellular Deproliferation Method

During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

20 µl of MTS was immediately added to the T0 wells and they were read 90 minutes after. T1 and T2 were treated with different concentrations (2.5 µM to 50 µM) of L-733,060 and were incubated during a varying period in cellular lines.

Line COLO 858: 48 h. (first cellular duplication) (T1) and 96 hrs. (second cellular duplication) (T2).

Line MEL HO: 24 hrs. (cellular duplication) (T1) and 48 hrs. (second cellular duplication) (T2).

Line COLO 679: 30 hrs. (cellular duplication) (T1) and 72 hrs. (second cellular duplication)(T2).

To study the cellular proliferation, 20 µl of reactive MTS was added to each well (T1, T2) 90 min. before reading the plate samples with the (TECAN Spectra Classic) 492 nm. the quantity of reactive MTS, the optical density was measured, being directly proportional to the number of live cells. Each plate (white, control, and control treated with different concentrations of L-733,060) was done in triplicate. The experiment was repeated on three different occasions. The concentrations to inhibit fifty percent of the cells (IC50) with L-733,060 was calculated on a curve suited to the parameters.

Statistical Analysis: The data obtained was evaluated using the Student's t-test, with a significance level of $P<0.05$.

Results: The results are shown in FIGS. 2A, 2B (COLO 858), FIGS. 3A and 3B (MEL HO) and FIGS. 4A and 4B (COLO 679).

Figure 2:
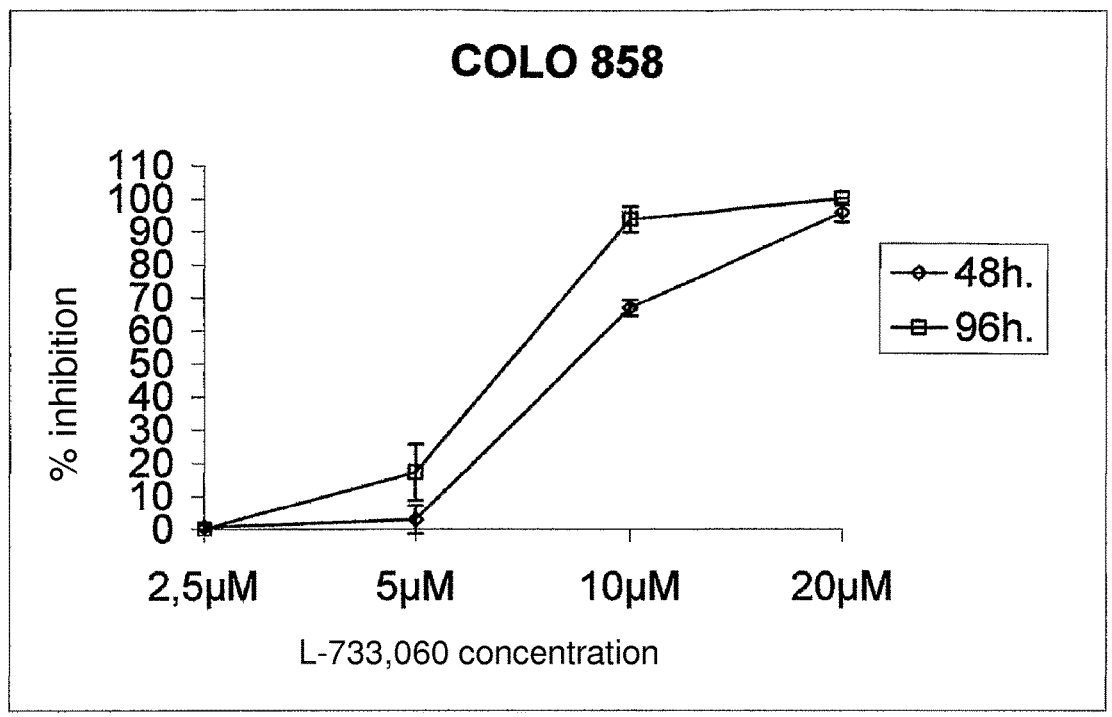
FIGS. 2A and 2B: variation in the time of the concentration of the cells COLO 858 to growing concentrations of L-733,060(2A) in the cellular growth inhibition of COLO 858 (2B).
Figure 2:
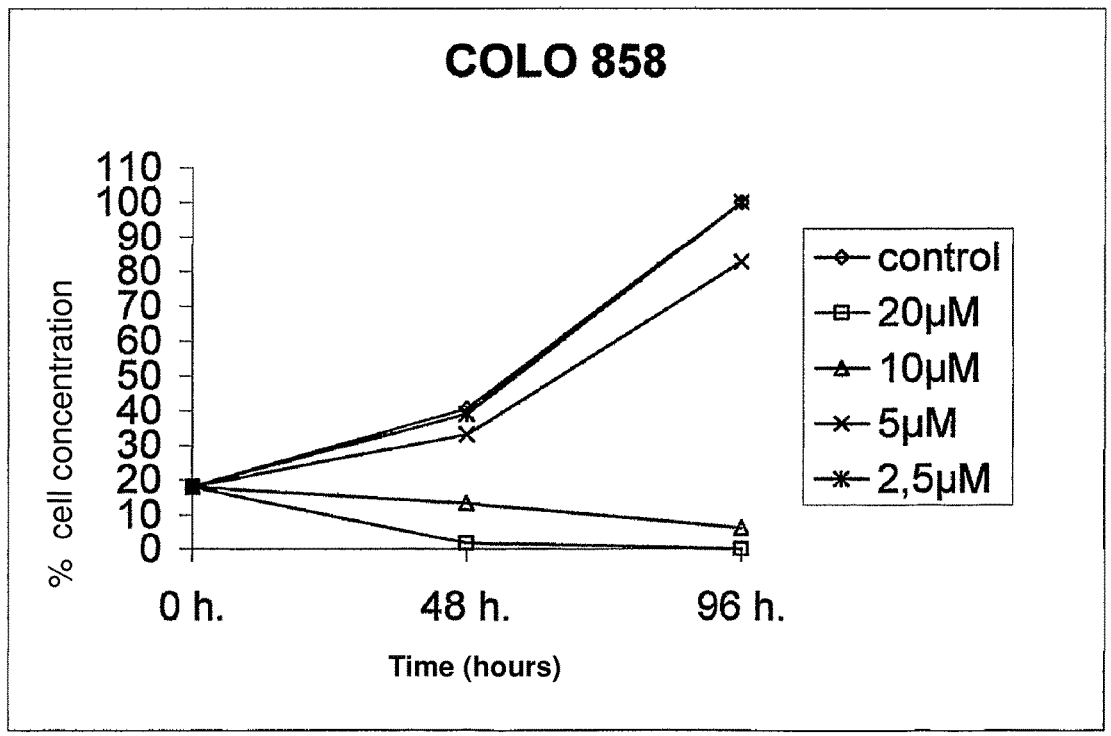

FIG. 2A represents the variation in the time of the concentration of cells COLO 858 to growing concentrations of L-733,060 (from 2.5 to 20 µm).

Figure 3:
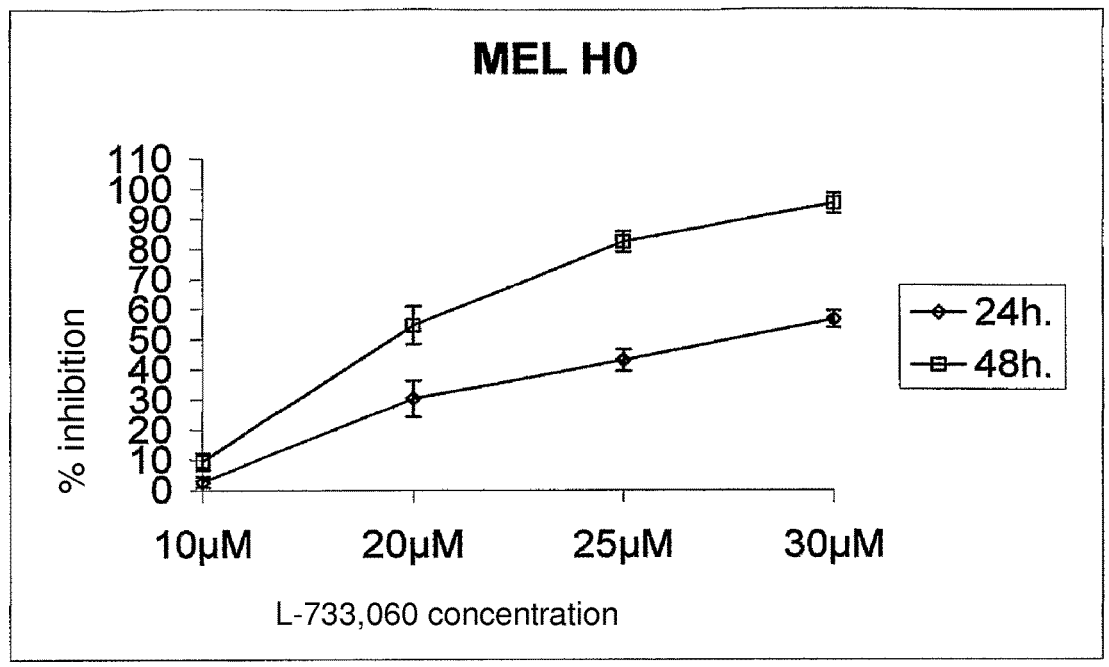
FIGS. 3A and 3B: variation in the time of the concentration of the cells MEL HO to growing concentrations of L-733,060 (3A) in the cellular growth inhibition of MEL HO (3B).
Figure 3:
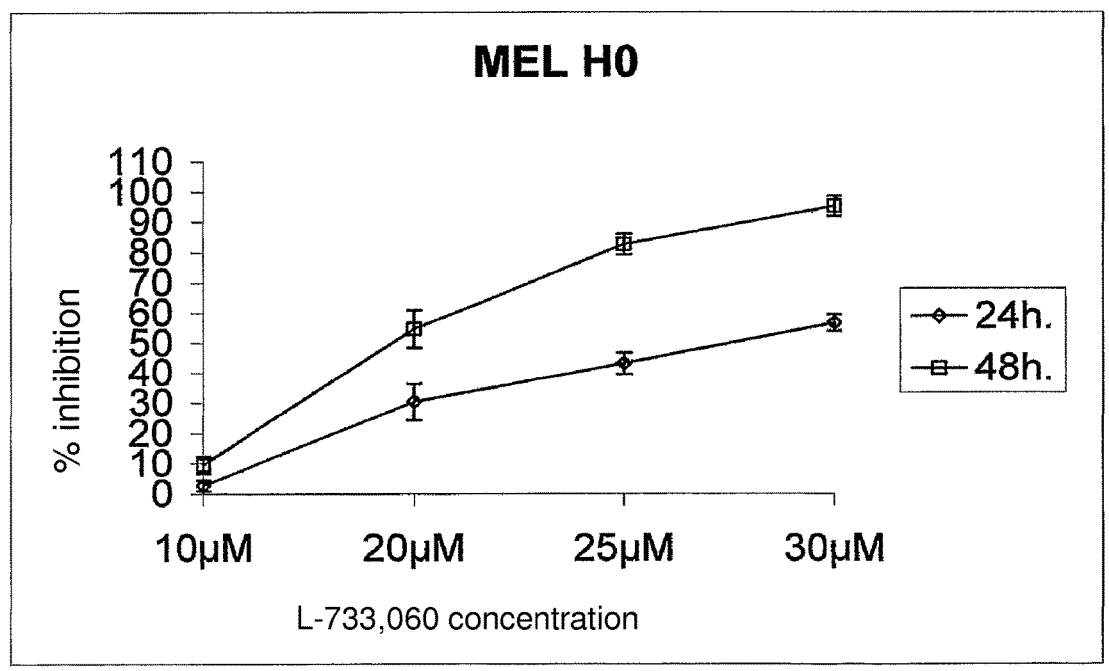

FIG. 3A represents the variation in the time of the concentration of cells MEL HO to growing concentrations of L-733,060(from 10 to 30 µM).

Figure 4:
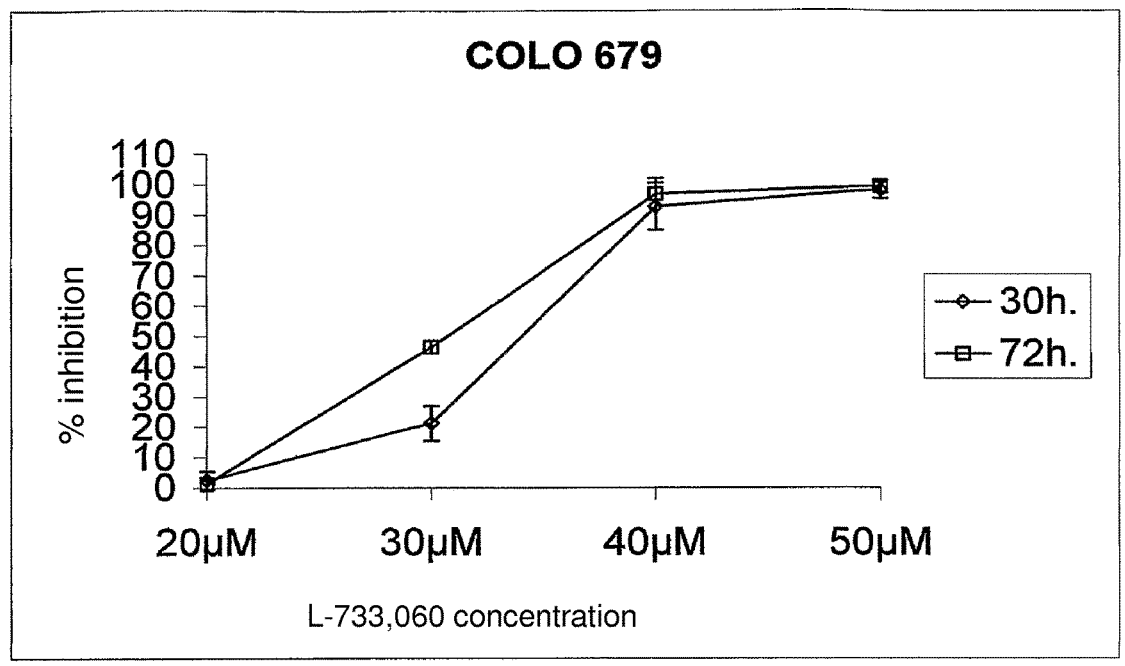
FIGS. 4A and 4B: variation in the time of the concentration of the cells COLO 679 to growing concentrations of L-733,060 (4A) in the cellular growth inhibition of COLO 679 (4B).
Figure 4:
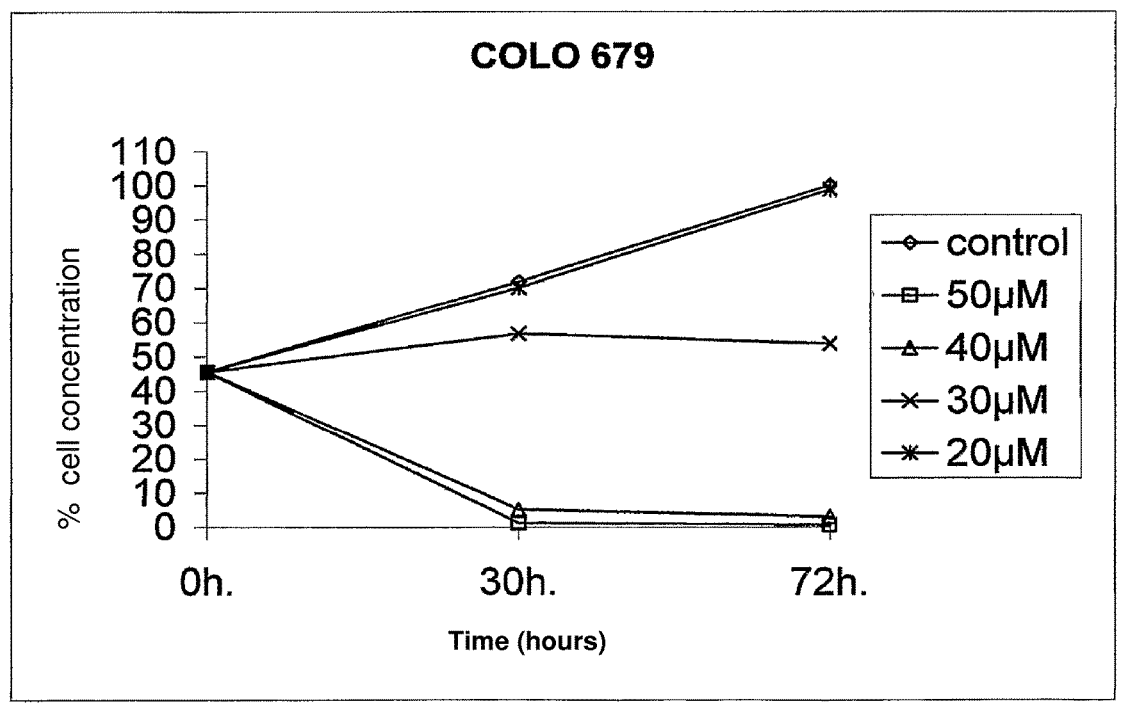

FIG. 4A represents the variation in the time of the concentration of cells COLO 679 to growing concentrations of L-733,060 (from 20 to 50 µM).

In FIG. 2B the inhibition of cellular growth is shown from COLO 858(at 48 and 96 hrs.) after the addition of growing concentrations of L-733,060 (2.5, 5, 10, 20 µM). The discontinuous lines represent the IC50 for 48 and 96 hrs. The points on the graph represent the value of the average value/typical deviation.

In FIG. 3B the inhibition of cellular growth is shown from MEL HO (at 24 and 48 hrs.) after the addition of growing concentrations of L-733,060 (10, 20, 25 and 30 µM). The discontinuous lines represent the IC50 for 24 and 48 hrs. The points on the graph represent the average value/typical deviation.

In FIG. 4B the inhibition of cellular growth is shown from COLO 679 (at 30 and 72 hrs. after the addition of growing concentrations of L-733,060 (20, 30, 40 and 50 µM). The discontinuous lines represent the IC50 for 30 and 72 hrs. The points on the graph represent the average value/typical deviation.

Example 3

Cellular lines related with lymphoblastic leukemia. Cellular lines related with human lymphoblastic leukemia have been used with BSD1 (DSMZ) and the cells T BE-13 (DSMZ).

These cellular lines were maintained in a culture of 1640 supplemented with 10% fetal bovine serum according to the established cellular culture conditions of the ATCC.

The cellular line was cultivated in flasks of 75 ml (Falcon, Germany). Half were renewed every two days. The cells were incubated at a temperature of 37 C in a humidification of (95% air/5% CO2).

Treatment with Antagonist NK1 Receptors

The solutions of the antagonist NK1 receptors (2S,3S) 3-([3,5-Bis(trifluoromethyl)phenyl]metoxi)-2-phenylpiperidine, (L-733,060) (Sigma-Aldrich, U. K.) were dissolved in distilled water containing 0.2% dimethyl sulfoxide (DMSO) before treating the samples. Different concentrations of (2.5 µM to at 25 µM) were studied in order to determine the IC50.

The cellular proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

Method of Cellular Proliferation

The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 µl of MTS was immediately added to the wells and they were read 90 minutes later. T1 and T2 were treated with different concentrations (2.5 µM to 20 µM) of L-733,060 and were incubated during a period of 30 hrs. (cellular duplication) (T1) and 72 hrs. (second cellular duplication) (T2).

To study the proliferation of the cells 20 µl of reactive MTS was added to each well (T1, T2) 180 min. before reading the samples with the plate reader (TECAN Spectra Classic) at 492 nm. The quantity of reactive MTS, was measured by optical density, being directly proportional in number of live cells. Each plate (white, control, and control treated with different concentrations of L-733,060) was done in triplicate. The experiment was repeated on three different occasions. The concentration to inhibit fifty percent of the cells (IC50) with L-733,060 was calculated with a curve suited to the parameters.

Statistical Analysis: The data obtained was evaluated using the Student's t-test, with a significance level of $P<0.05$.

Figure 5:
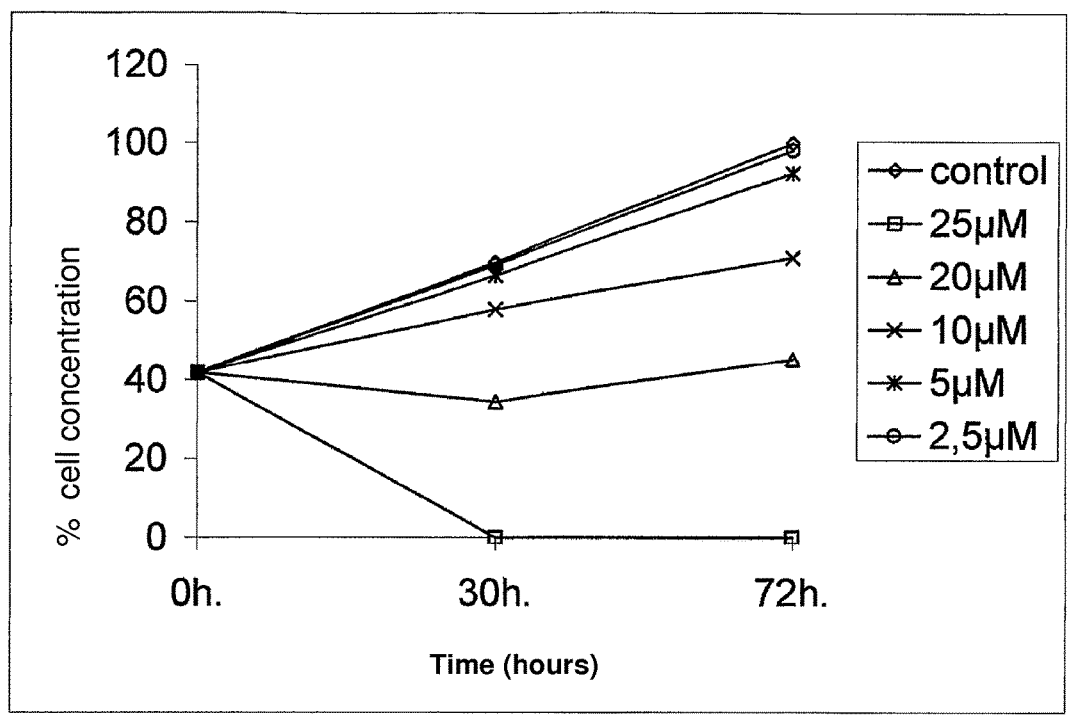
FIG. 5: variation in the time of the concentration of the cells SD1 to growing concentrations of L-733,060 in the cellular growth inhibition of SD1.

Results: The results shown in FIG. 5 represents the variation in time of the concentration of cells B SD1 to growing concentrations of L-733,060.

Example 4

Cellular lines related with Burkitt's human lymphoma The cellular line of Burkitt's human lymphoma was used with CA-46 (DSMZ).

This cellular line was maintained in a culture of RPMI 1640 supplemented with 10% fetal bovine serum according to the established cellular culture conditions of the ATCC.

The cellular lines were cultivated in flasks of 75 ml (Falcon, Germany). Half was renewed every two days and the cells were treated with Trypsin (0.05% and 0.02% EDTA in Ca2+ and Mg2+) every six days. The cells were incubated at 37 C in a humidification of (95% air/5% CO2).

Treatment with NK1 receptor antagonists The solutions of the NK1 receptor antagonists (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 25 µM) were studied to determine the IC50 IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

The discontinuous lines represent the IC50 at 30 and 72 hrs. The points on the graph show the average value/typical deviation.

Method of Cellular Proliferation

The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 µL of MTS was immediately added to the wells and they were read 90 minutes later. T1 and T2 were treated with different concentrations (2.5 µM to 25 µM) of L-733,060 and were incubated during a period of 35 hrs. (cellular duplication) (T1) and 72 hrs. (second cellular duplication) (T2).

To study the proliferation of the cells 20 pi of reactive MTS was added to each well (T1, T2) 90 min before reading the samples with the plate reader (TECAN Spectra Classic) at 492 nm. The quantity of reactive MTS was measured by optical density, being directly proportional in number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on a curve suited to the parameters.

Statistical Analysis: The data obtained was evaluated using the Student's t-test, with a significance level of $P<0.05$.

Results: At the highest concentrations, inhibition in cellular growth was produced and at the maximum dose, apoptosis.

Example 5

Cellular lines related with human Hodgkin's lymphoma. Cellular lines related with human Hodgkin's lymphoma. KM-H2 (DSMZ) were used.

This cellular line was maintained in a culture of RPMI 1640 and supplemented with 10% fetal bovine serum according to the established cellular culture conditions of the ATCC.

The cellular line was cultivated in flasks of 75 ml (Falcon, Germany). Half were renewed every two days. The cells were incubated at a temperature of 37 C in a humidification of (95% air/5% CO2).

Treatment with NK1 receptor antagonists The solutions of the NK1 receptor antagonists (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 25 µM) were studied to determine the IC50 IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

Method of Cellular Proliferation

The cells were quantified and cultured in plates of 96 wells each. Each experiment included three plates termed T0, T1 and T2.

T0 contained wells without cells (0 cells/0.1 ml) termed white wells and wells that contained cells ($10^4$ cells./0.1 ml) were termed control wells. Both, T1 and T2, included white wells (0 cells/0.1 ml), control wells ($10^4$ cells/0.1 ml) and control wells treated with L-733,060.

In T0, 20 µl of MTS was immediately added to the wells and they were read 90 minutes later. T1 and T2 were treated with different concentrations (2.5 µM to 20 µM) of L-733,060 and were incubated during a period of 48 hrs. (cellular duplication) (T1) and 96 hrs. (second cellular duplication) (T2).

To study the proliferation of the cells 20 µL of reactive MTS was added to each well (T1, T2) 180 min. before reading the samples with the plate reader (TECAN Spectra Classic) at 492 nm. The quantity of reactive MTS, was measured by optical density, being directly proportional in number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on a curve suited to the parameters.

The data obtained was evaluated using the Student's t-test, with a significance level of $P<0.05$.

Results: The results shown in FIG. 6A represent the variation in the time of the concentration of the cells KM-H2 with growing concentrations of L-733,060.

Figure 6:
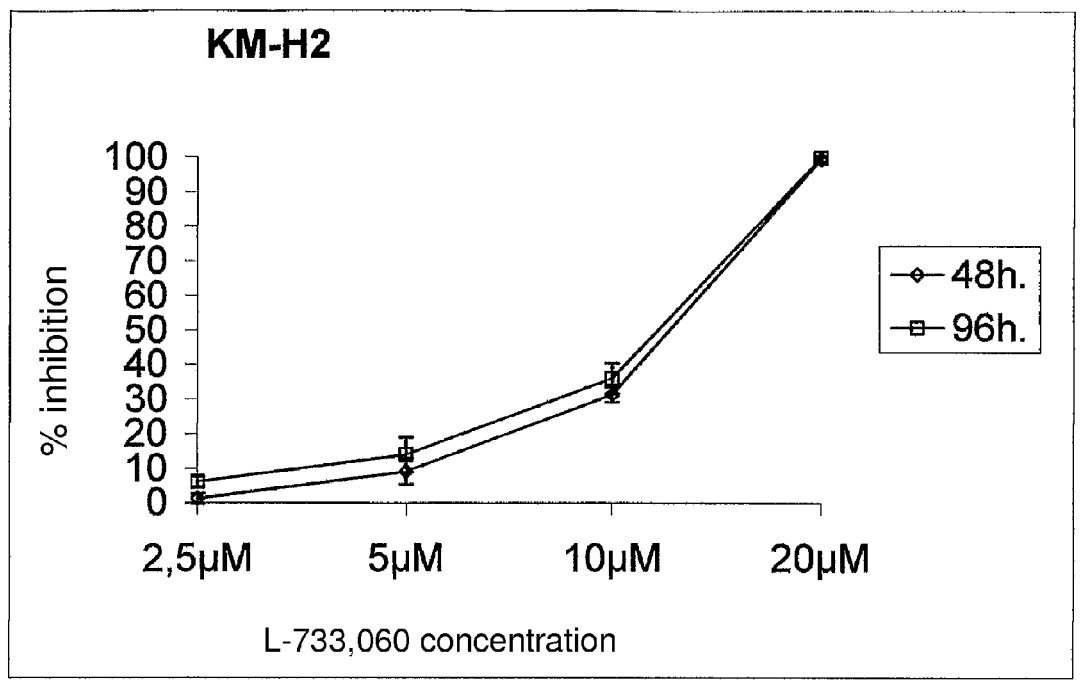
FIGS. 6A and 6B: variation in the time of the concentration of the cells KM-H2 to growing concentrations of L-733,060 (6A) in the cellular growth inhibition of KM-H2 (6B).
Figure 6:
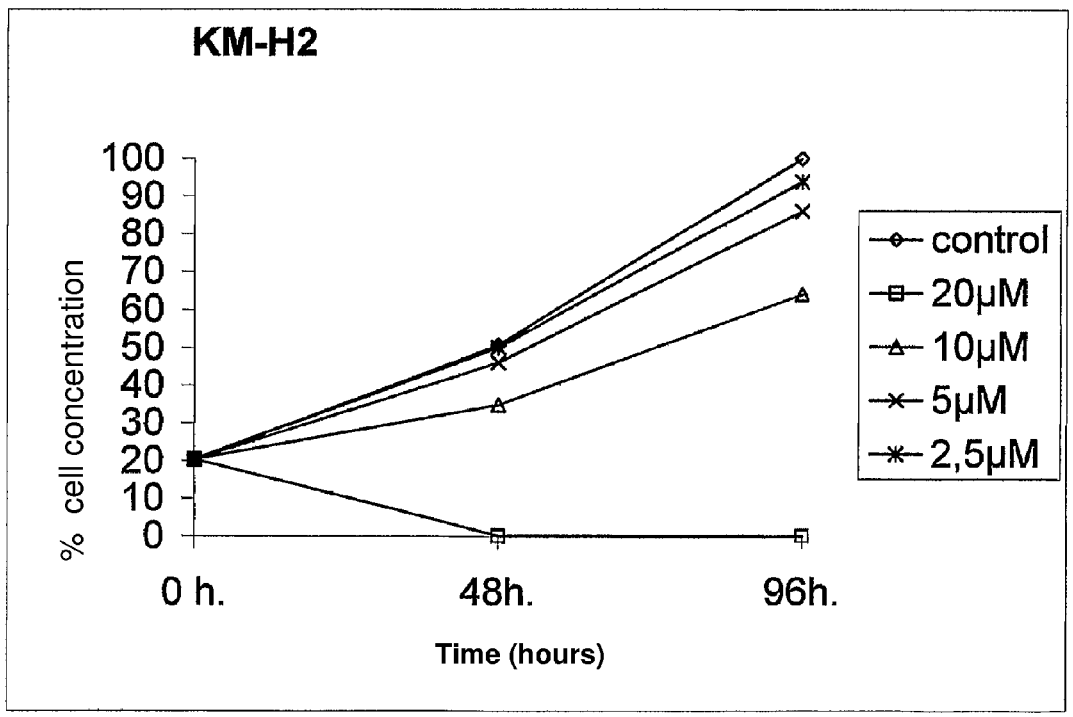

In FIG. 6B the inhibition of cell growth KM-H2 is represented (at 48 and 96 hrs.) after the addition of growing concentrations of L-733,060 (2.5, 5, 10, 20 µM). The percentage of the inhibition for the first and second time of the duplication of the incubation. The discontinuous lines represent the IC50 at 48 and 96 hrs. The points on the graph represent the average value/typical deviation.

Example 6

Cellular Lines Related to Human Rhabdomyosarcoma.

Cellular Lines Related to Human Rhabdomyosarcoma A-204 (DSMZ) were Used.

This cellular line was maintained in a culture of Mc-Co- supplemented with 10% fetal bovine serum according to the established cellular culture conditions of the ATCC.

The cellular line was cultivated in flasks of 75 ml (Falcon, Germany). Half were renewed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with antagonist NK1 receptors The solutions of the antagonist NK1 receptors (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 25 µM) were studied to determine the IC50 IC50.

The cell proliferation was evaluated using the MTS method [3-(4,5-dimethylthiazol-2il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

Method of Cellular Proliferation

During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 µl of MTS was immediately added to the wells and were read 90 minutes later. T1 and T2 were treated with different concentrations (2.5 µM to 20 µM) of L-733,060 and were incubated during a period of 36 hrs. (first cellular duplication) (T1) and 72 hrs. (second cellular duplication) (T2).

To study the proliferation of the cells 20 µl of MTS reactor was added to each well (T1, T2) 90 min., before reading the samples with the plate reader (TECAN Spectra Classic) at 492 nm. The reactive quantity of MTS, was measured by testing the optical density, being directly proportional to the number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on an adequate curve based on the parameters.

Statistical Analysis: The data obtained was evaluated using the Student's t-test, with a significance level of $P<0.05$.

Results: Cellular growth is inhibited at the highest concentrations and at the maximum dose, apoptosis.

Example 7

Cellular Lines Related with Small Cell Lung Cancer

Cellular lines related with small cell lung cancer COLO-677 (DSMZ) was used. This cellular line was maintained in a culture of RPMI 1640 supplemented with 10% fetal bovine serum according to the established cellular culture conditions of the ATCC.

The cellular line was cultivated in flasks of 75 ml (Falcon, Germany). Half were renewed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with antagonist NK1 receptors The solutions of the antagonist NK1 receptors (2S,3S) 3-[(3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 25 µM) were studied to determine the IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

Method of Cellular Proliferation

During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 µl of MTS was immediately added to the wells and they were read 90 minutes later. T1 and T2 were treated with different concentrations (5 µM to 20 µM) of L-733,060 and were incubated during a period of 40 hrs. (first cellular duplication) (T1) and 96 hrs. (second cellular duplication) (T2).

To study the proliferation of the cells 20 µL of MTS reactor was added to each well (T1, T2) 90 min., before reading the samples with the plate reader (TECAN Spectra Classic) at 492 nm. The reactive quantity of MTS, was measured by testing the optical density, being directly proportional to the number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on an adequate curve based on the parameters.

Statistical Analysis: The data obtained was evaluated using the Student's t-test, with a significance level of $P<0.05$. Results: Cellular growth is inhibited at the highest concentrations and at the maximum dose, apoptosis.

Example 8

Cellular lines related with human breast cancer Cellular lines related with human breast cancer MT-3 (DSMZ) was used. This cellular line was maintained in a culture of RPMI 1640 supplemented with 10% fetal bovine serum according to the established cellular culture conditions of the ATCC.

The cellular line was cultivated in flasks of 75 ml (Falcon, Germany). Half were renewed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with NK1 receptor antagonists The solutions of the NK1 receptor antagonists (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 25 µM) were studied to determine the IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

Method of Cellular Proliferation

During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both T1 and T2, included white wells (0 cells/0.1 ml), control wells ($10^4$ cells/0.1 ml) and control wells treated with L-733,060.

In T0, 20 µl of MTS was immediately added to the wells and they were read 90 minutes later. T1 and T2 were treated with different concentrations (2.5 µM to 20 µM) of L-733,060 and were incubated during a period of 30 hrs. (first cellular duplication) (T1) and 72 hrs. (second cellular duplication) (T2).

To study the proliferation of the cells 20 pi of reactive MTS was added to each well (T1, T2) 90 min before reading the samples with the plate reader (TECAN Spectra Classic) at 492 nm. The quantity of reactive MTS, was measured by optical density, being directly proportional in number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on a curve suited to the parameters.

Statistical Analysis: The data obtained was evaluated using the Student's t-test, with a significance level of $P<0.05$.

Results: The results shown in FIG. 7A represent the variation in the time of the concentration of cells MT-3 at growing concentrations of L-733,060.

Figure 7:
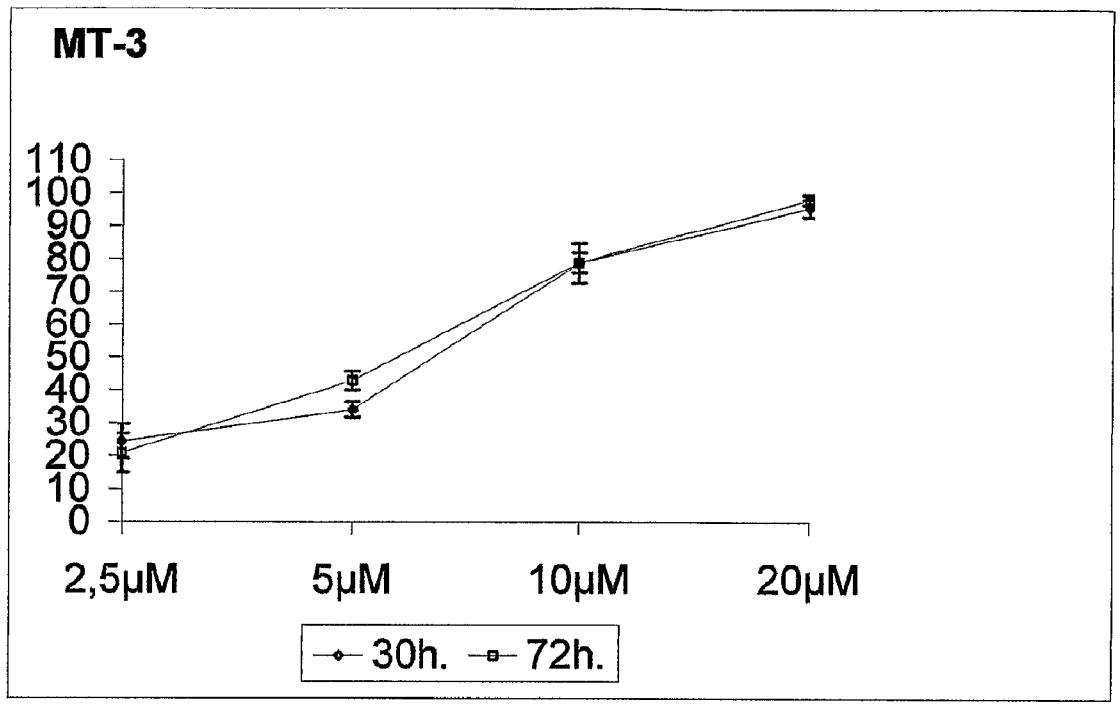
FIGS. 7A and 7B: variation in the time of the concentration of the cells MT-3 to growing concentrations of L-733,060 (7A) in the cellular growth inhibition of MT-3 (7B).
Figure 7:
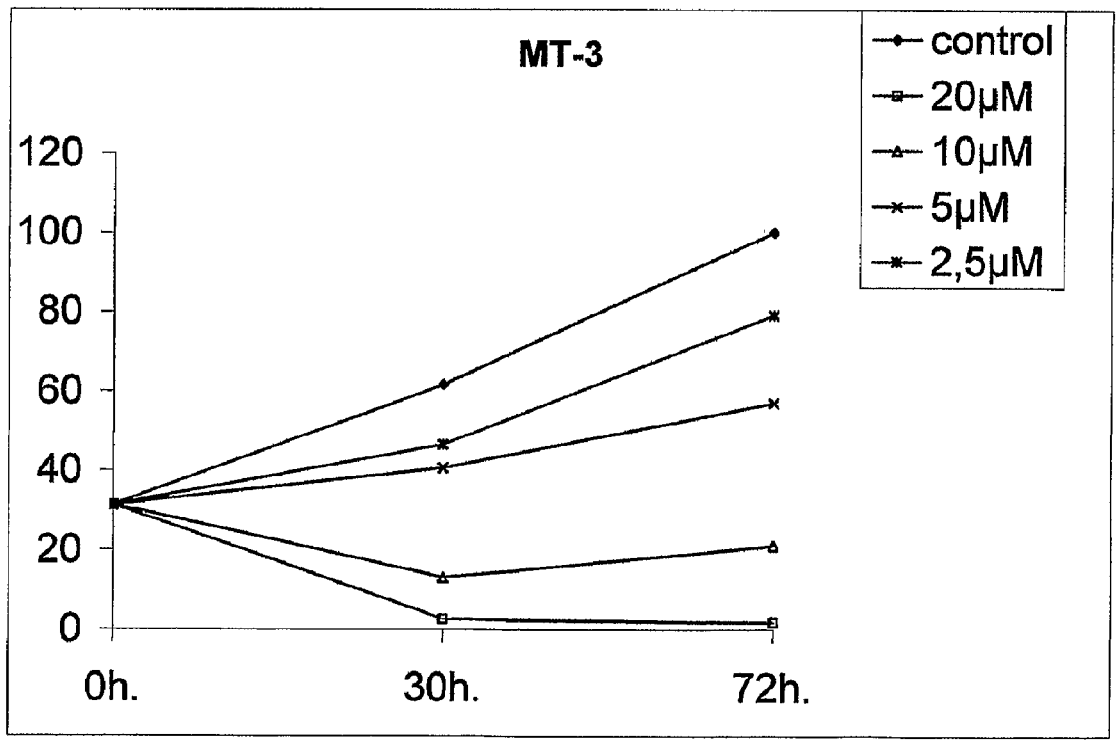

In FIG. 7B the inhibition of cell growth MT-3 is represented (at 30 and 72 hrs.) after the addition of growing concentrations of L-733,060 (2.5, 5, 10, 20 µM). The percentage of the inhibition for the first and second time in the duplication of the incubation. The discontinuous lines represent the IC50 at 30 and 72 hrs. The points on the graph represent the average value/typical deviation.

Example 9

Cellular lines related to Edwing's human sarcoma Cellular lines related to Edwing's human sarcoma MHH-ES-1 (DSMZ) were used. This cellular line was maintained in a culture of RPMI 1640 supplemented with 10% fetal bovine serum according to the established cellular culture conditions of the ATCC.

The cellular line was cultivated in flasks of 75 ml (Falcon, Germany). Half were renewed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with NK1 receptor antagonists The solutions of the NK1 receptor antagonists (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 µM to 25 µM) were studied to determine the IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA).

Method of Cellular Proliferation

During the experiment, the cultivated cells were broken apart every 4-5 days by way of tripsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells./0.1 ml)

were termed control wells. Both, T1 and T2, included white wells (0 cells/0.1 ml), control wells ($10^4$ cells/0.1 ml) and control wells treated with L-733,060.

In T0, 20 Pl of MTS was immediately added to the wells and they were read 90 minutes later. T1 and T2 were treated with different concentrations (5 μM to 20 μM) of L-733,060 and were incubated during a period of 30 hrs. (first cellular duplication) (T1) and 72 hrs. (second cellular duplication) (T2).

To study the proliferation of the cells 20 μl of reactive MTS was added to each well (T1, T2) 90 min before reading the samples with the plate reader (TECAN Spectra Classic) at 492 nm. The quantity of reactive MTS, was measured by optical density, being directly proportional in number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on a curve suited to the parameters.

Statistical Analysis: The data obtained was evaluated using the Student's t-test, with a significance level of $P<0.05$.

Results: The results shown in FIG. 8A represent the variation in the time of the concentration of cells MHH-ES-1 at growing concentrations of L-733,060.

Figure 8:
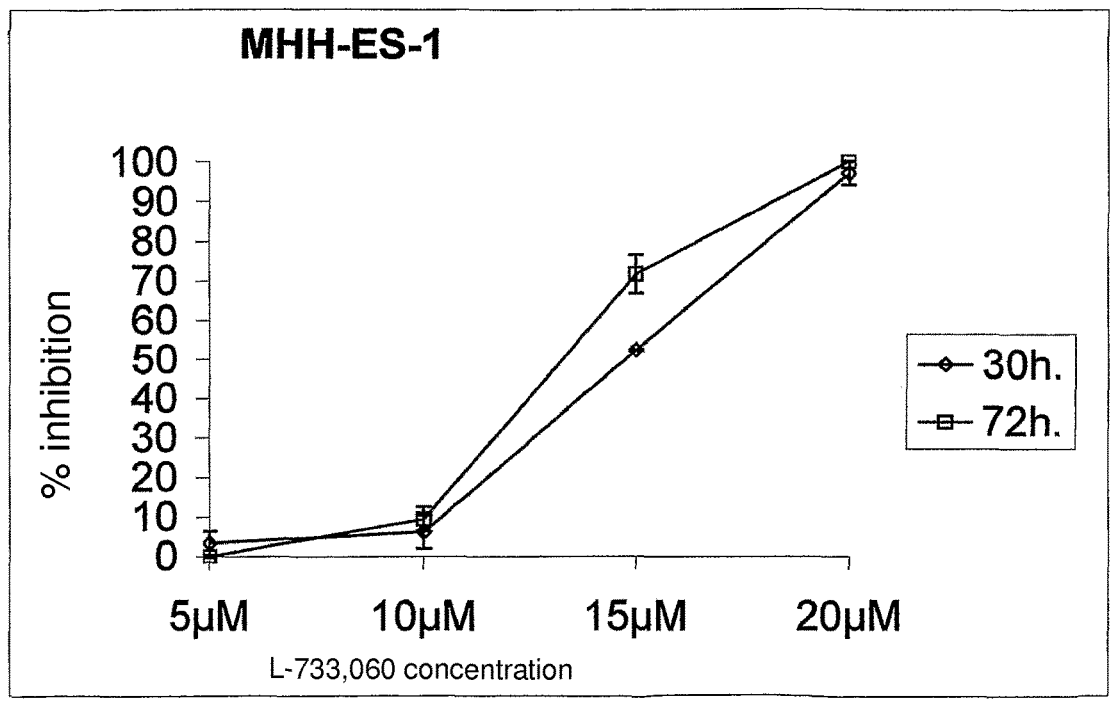
FIGS. 8A and 8B: variation in the time of the concentration of the cells MHH-ES-1 to growing concentrations of L-733,060 (8A) in the cellular growth inhibition of MHH-ES-1 (8B).
Figure 8:
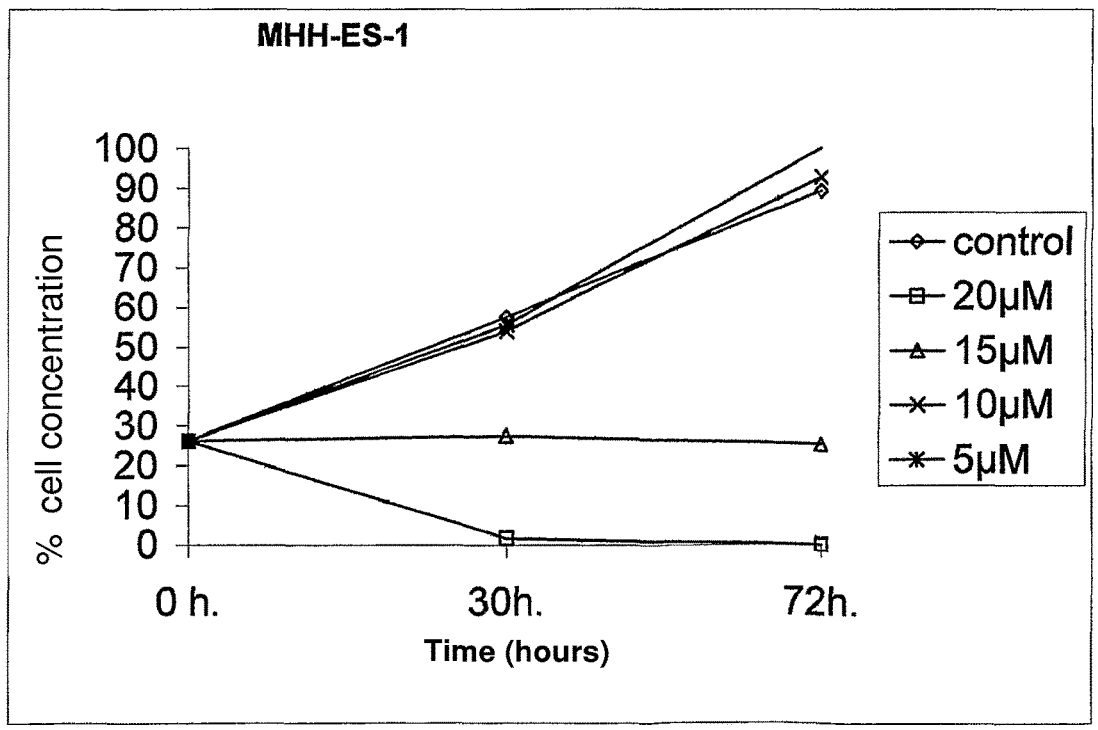

In FIG. 8B the inhibition of cell growth MHH-ES—1 is represented (at 30 and 72 hrs.) after the addition of growing concentrations of L-733,060 (5, 10, 15, 20 μM). The percentage of the inhibition for the first and second time of the duplication of the incubation. The discontinuous lines represent the IC50 at 30 and 72 hrs. The points on the graph represent the average value/typical deviation.

Example 10

Cellular line related to human osteosarcoma Cellular lines related to human osteosarcoma MG-63 (ICLC) were used.

This cellular line was maintained in a culture of MEN supplemented with 10% fetal bovine serum according to the established cellular culture conditions of the ATCC.

The cellular line was cultivated in flasks of 75 ml (Falcon, Germany). Half were renewed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with NK1 receptor antagonists The solutions of the NK1 receptor antagonists (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 μM to 25 μM) were studied to determine the IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA). Method of Cellular Proliferation During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 μl of MTS was immediately added to the wells and they were read 90 minutes after. T1 and T2 were treated with different concentrations (2.5 μM to 25 μM) of L-733,060 and were incubated during a period of 30 hrs. (one cellular duplication) (T1) and 72 hrs. (second cellular duplication)(T2)

To study the proliferation of the cells 20 μl of reactive MTS was added to each well (T1, T2) 90 min before reading the samples with the plate reader (TECAN Spectra Classic) at 492 nm. The quantity of reactive MTS, was measured by optical density, being directly proportional to the number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on a curve suited to the parameters.

Statistical Analysis: The data obtained was evaluated using the Student's t-test, with a significance level of $P<0.05$.

Figure 9:
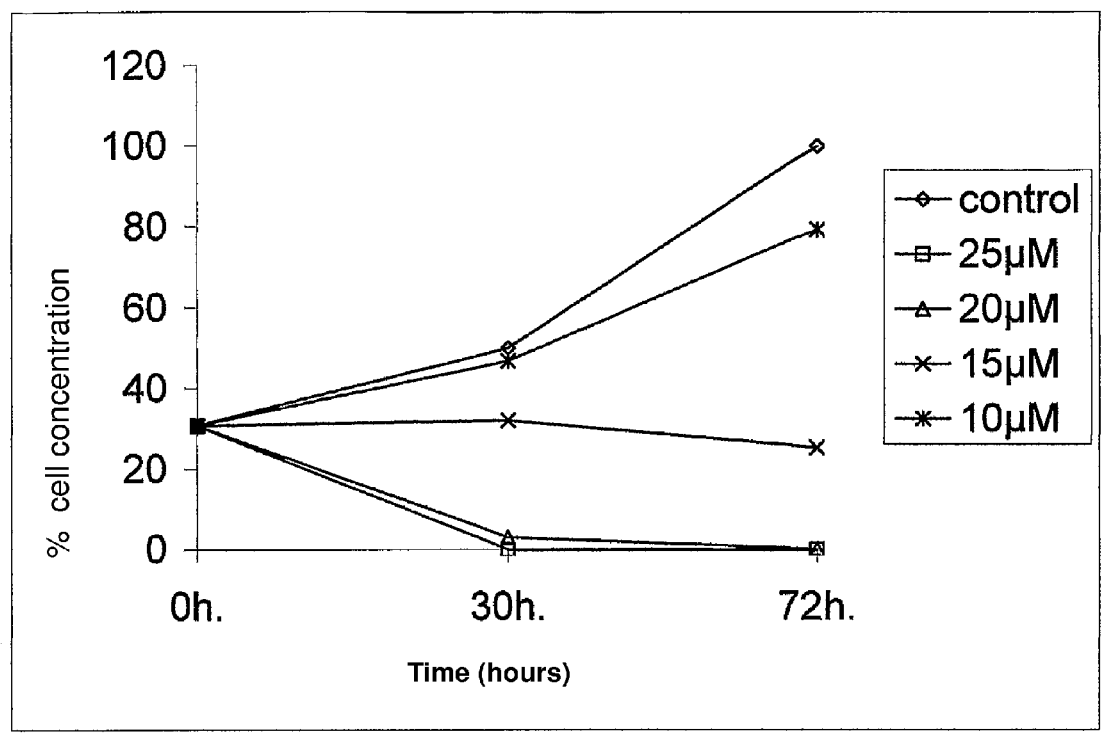
FIG. 9: variation in the time of the concentration of the cells MG-63 to growing concentrations of L-733,060 in the cellular growth inhibition of MG-63.

Results: The results shown in FIG. 9 represent the variation in the time of the concentration of cells at growing concentrations of L-733,060.

Example 11

Cellular lines related to glioma Cellular lines related to human glioma GAMG (DSMZ) was used.

This cellular line was maintained in a culture of MEN supplemented with 10% fetal bovine serum according to the established cellular culture conditions of the ATCC.

The cellular line was cultivated in flasks of 75 ml (Falcon, Germany). Half were renewed every two days and the cells were treated with Trypsin (0.05% and 0.02% EDTA without Ca2+ and Mg2+) every six days. The cells were incubated at a temperature of 37 C in a humidification of (95% air/5% CO2).

Treatment with NK1 receptor antagonists The solutions of the NK1 receptor antagonists (2S,3S) 3-([3,5-Bis(trifluoromethyl)phenyl]metoxi)-2-phenylpiperidine, (L-733,060) (Sigma-Aldrich, U.K.) were dissolved in distilled water containing 0.2% dimethyl sulfoxide (DMSO) before treating the samples. Different concentrations of (2.5 μM to 25 μM) were studied to determine the IC50.

The cell proliferation was evaluated using the MTS method [3-(4,5-dimethylthiazol-2-il)-5-(3-carboxymethoxyphenyl) 2-(4-sulfophenyl)-2H-tetrazolium], following the instructions of use by the manufacturer (CellTiter 96 Aqueous One Solution Cell Proliferation Assay, Promega, USA). Method of Cellular Proliferation During the experiment, the cultivated cells were broken apart every 4-5 days by way of trypsinization and to test the cell viability the blue trypan method was used. The cells were quantified and cultured in plates of 96 wells each. Each experiment included three plates termed T0, T1 and T2.

T0 contained wells without cells (0 cells/0.1 ml) termed white wells and wells that contained cells ($10^4$ cells/0.1 ml) were termed control wells. Both, T1 and T2, included white wells (0 cells/0.1 ml), control wells ($10^4$ cells/0.1 ml) and control wells treated with L-733,060.

In T0, 20 μl of MTS was immediately added to the wells and they were read 90 minutes later. T1 and T2 were treated with different concentrations (2.5 μM to 25 μM) of L-733, 060 and were incubated during a period of 48 hrs. (first cellular duplication) (T1) and 96 hrs. (second cellular duplication) (T2).

To study the proliferation of the cells 20 µl of reactive MTS was added to each well (T1, T2) 90 min before reading the samples with the plate reader (TECAN Spectra Classic) at 492 nm. The quantity of reactive MTS, was measured by optical density, being directly proportional in number of live cells. Each plate (white, control, and control treated with different concentrations of L-733,060) was done in triplicate. The experiment was repeated on three different occasions. The concentration to inhibit fifty percent of the cells (IC50) with L-733,060 was calculated on a curve suited to the parameters.

Statistical Analysis. The data obtained was evaluated using the Student's t-test, with a significance level of $P<0.05$.

Results: The results shown in FIG. 10A represent the variation in the time of the concentration of cells at growing concentrations of L-733,060.

Figure 10:
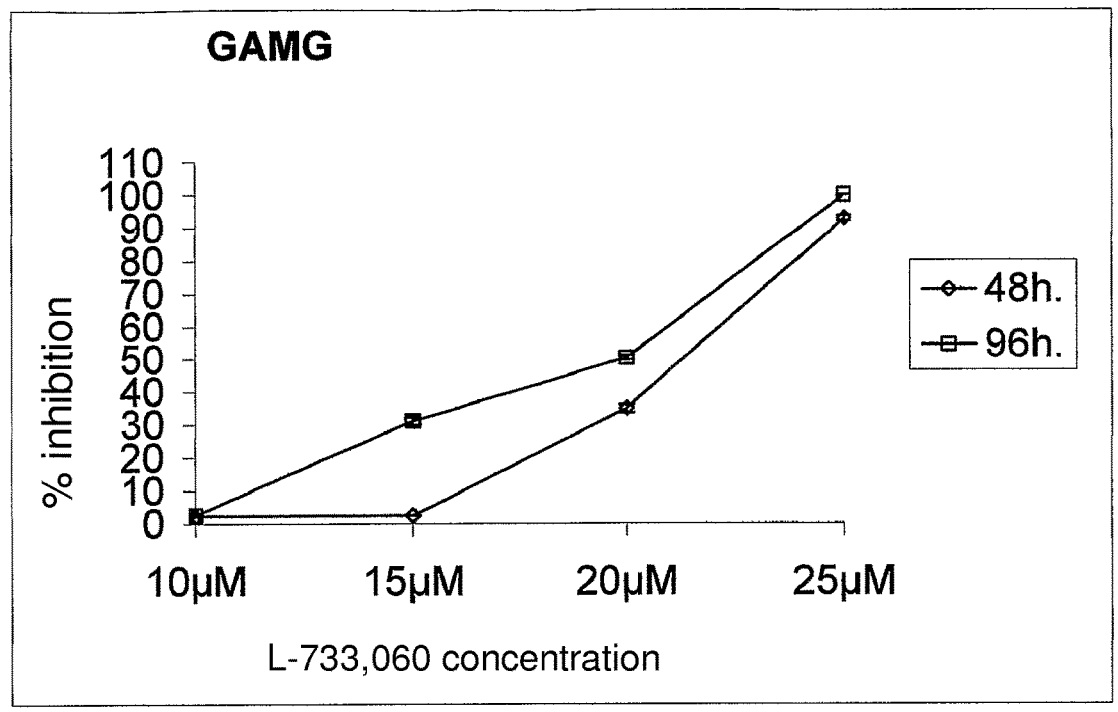
FIGS. 10A and 10B: variation in the time of the concentration of the cells GAMG to growing concentrations of L-733,060 (10A) in the cellular growth inhibition of GAMG (10B).
Figure 10:
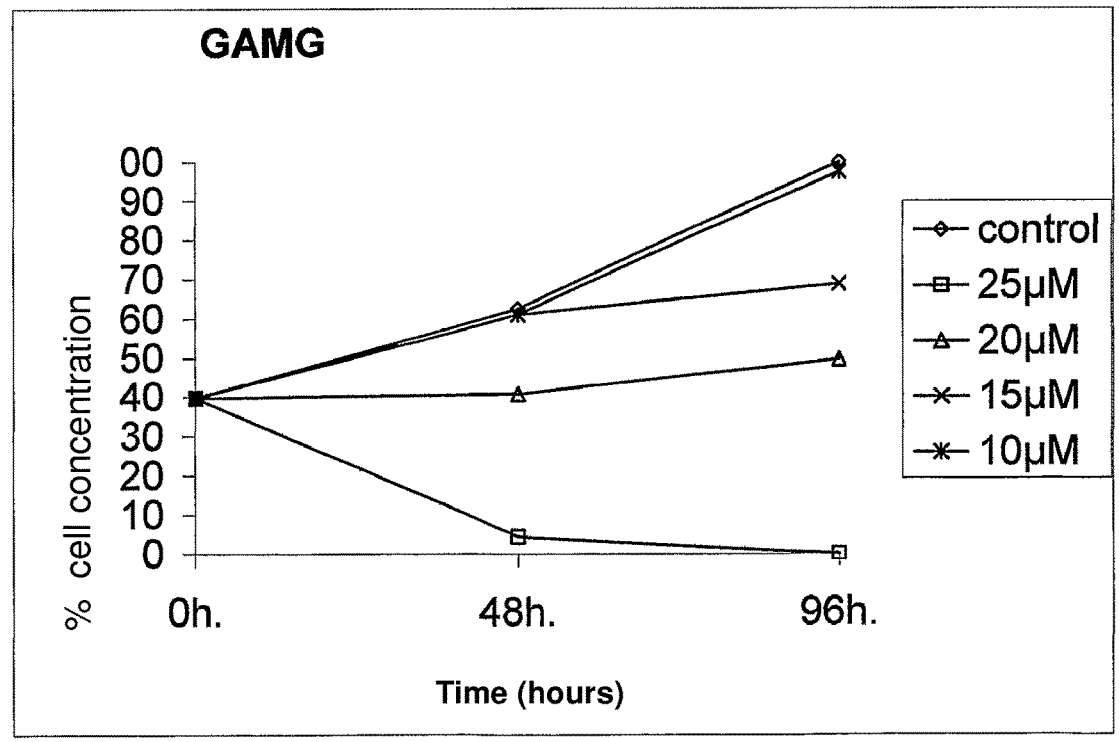

In FIG. 10B the inhibition of cell growth GAMG is represented (at 48 and 96 hrs.) after the addition of growing concentrations of L-733, 060 (10, 15, 20 and 25 µM). The percentage of the inhibition for the first and second time of the duplication of the incubation. The discontinuous lines represent the IC50 at 30 and 72 hrs. The points on the graph represent the average value/typical deviation.

What is claimed is:

1. A method of inducing apoptosis in melanoma cells comprising contacting the melanoma cells with a non-peptide NK1 receptor antagonist in an amount effective to induce apoptosis, wherein the non-peptide NK1 receptor antagonist is (2S,3S)3-{[3,5-Bis(trifluoromethyl)phenyll-metoxi}-2-phenylpiperidine (L-733060) or aprepitant, wherein the melanoma cells comprise a level of NK1 receptors that is 400% to 500% of the level on non-tumor cells.

2. The method of claim 1, wherein the melanoma cells are in a human subject.

3. A method of treating melanoma in a human subject comprising administering a therapeutically effective amount of a non-peptide NK1 receptor antagonist, wherein the non-peptide NK1 receptor antagonist is (2S,3S)3-{[3,5-Bis(trifluoromethyl)phenyllmetoxi}-2-phenylpiperidine (L-733060) or aprepitant, wherein the melanoma cells comprise a level of NK1 receptors that is 400% to 500% of the level on non-tumor cells.

4. The method of claim 3, wherein the non-peptide NK1 receptor antagonist is administered in an amount effective to induce apoptosis of melanoma cells.

* * * * *

UNITED STATES PATENT AND TRADEMARK OFFICE
CERTIFICATE OF CORRECTION

PATENT NO. : 9,867,814 B2
APPLICATION NO. : 11/721256
DATED : January 16, 2018
INVENTOR(S) : Miguel Munoz Saez It is certified that error appears in the above-identified patent and that said Letters Patent is hereby corrected as shown below:

In the Specification

In Column 3, Lines 30-31, "(2S,3S) 3-{[3,5-Bis(trifluoromethyl)phenyl]metoxi}-2-phenylpiperidine" should read --(2S,3S) 3-{[3,5-Bis(trifluoromethyl)phenyl]methoxy}-2-phenylpiperidine--;

In Column 4, Lines 45-46, "(2S,3S)3-([3,5-Bis(trifluoromethyl)phenyl]metoxi)-2-phenylpiperidine" should read --(2S,3S)3-([3,5-Bis(trifluoromethyl)phenyl]methoxy)-2-phenylpiperidine--;

In Column 5, Lines 49-51, "(2S,3S) 3-([3,5 Bis(trifluoromethyl)phenyl]metoxi)-2-phenylpiperidine" should read --(2S,3S) 3-([3,5 Bis(trifluoromethyl)phenyl]methoxy)-2-phenylpiperidine--;

In Column 7, Lines 9-11, "(2S,3S) 3-([3,5-Bis(trifluoromethyl)phenyl]metoxi}-2-phenylpiperidine" should read --(2S,3S) 3-([3,5-Bis(trifluoromethyl)phenyl]methoxy}-2-phenylpiperidine--;

In Column 7, Line 67 to Column 8, Line 1, "(2S,3S) 3-([3,5-Bis(trifluoromethyl)phenyl]metoxi)-2-phenylpiperidine" should read --(2S,3S) 3-([3,5-Bis(trifluoromethyl)phenyl]methoxy)-2-phenylpiperidine--;

In Column 8, Lines 62-63, "(2S,3S) 3-([3,5-Bis(trifluoromethyl)phenyl]metoxi)-2-phenylpiperidine" should read --(2S,3S) 3-([3,5-Bis(trifluoromethyl)phenyl]methoxy)-2-phenylpiperidine--;

In Column 9, Lines 60-61, "(2S,3S) 3-([3,5-Bis(trifluoromethyl)phenyl]metoxi)-2-phenylpiperidine" should read --(2S,3S) 3-([3,5-Bis(trifluoromethyl)phenyl]methoxy)-2-phenylpiperidine--;

In Column 10, Lines 57-58, "(2S,3S) 3-([3,5-Bis(trifluoromethyl)phenyl]metoxi)-2-phenylpiperidine" should read --(2S,3S) 3-([3,5-Bis(trifluoromethyl)phenyl]methoxy)-2-phenylpiperidine--;

In Column 11, Lines 48-49, "(2S,3S) 3-([3,5-Bis(trifluoromethyl)phenyl]metoxi)-2-phenylpiperidine" should read --(2S,3S) 3-([3,5-Bis(trifluoromethyl)phenyl]methoxy)-2-phenylpiperidine--.

Signed and Sealed this
Twentieth Day of March, 2018

Andrei Iancu
*Director of the United States Patent and Trademark Office*